United States Patent
Ono et al.

(10) Patent No.: US 10,117,833 B2
(45) Date of Patent: Nov. 6, 2018

(54) METHOD FOR PRODUCING LIPOSOME

(71) Applicant: FUJIFILM Corporation, Tokyo (JP)

(72) Inventors: Makoto Ono, Ashigarakami-gun (JP);
Kohei Ono, Ashigarakami-gun (JP);
Yuuko Igarasi, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 15/336,131

(22) Filed: Oct. 27, 2016

(65) Prior Publication Data
US 2017/0042812 A1   Feb. 16, 2017

Related U.S. Application Data

(63) Continuation of application No. PCT/JP2015/062985, filed on Apr. 30, 2015.

(30) Foreign Application Priority Data

Apr. 30, 2014 (JP) ................. 2014-094142

(51) Int. Cl.
*A61K 9/127* (2006.01)
*A61K 47/10* (2017.01)
(Continued)

(52) U.S. Cl.
CPC ........... *A61K 9/127* (2013.01); *A61K 8/14* (2013.01); *A61K 9/1271* (2013.01); *A61K 9/1277* (2013.01); *A61K 31/7068* (2013.01); *A61K 47/10* (2013.01); *A61K 47/14* (2013.01); *A61Q 19/00* (2013.01); *B01J 13/125* (2013.01);
(Continued)

(58) Field of Classification Search
CPC ..................................................... A61K 9/127
See application file for complete search history.

(56) References Cited

U.S. PATENT DOCUMENTS

| | | | |
|---|---|---|---|
| 5,049,322 A | 9/1991 | Devissaguet et al. | |
| 5,174,930 A | 12/1992 | Stainmesse et al. | |

(Continued)

FOREIGN PATENT DOCUMENTS

| | | | |
|---|---|---|---|
| JP | 07-068119 B2 | 12/1985 | |
| JP | 08-024840 B2 | 6/1990 | |

(Continued)

OTHER PUBLICATIONS

Cortesi et al. (2008). "Preparation of liposomes by reverse-phase evaporation using alternative organic solvents." Journal of Microencapsulation, 16(2): 251-256.*

(Continued)

*Primary Examiner* — Isaac Shomer
(74) *Attorney, Agent, or Firm* — Sughrue Mion, PLLC (57) ABSTRACT

Provided is a method for producing a liposome having safety and stability. According to the present invention, it is possible to provide a method for producing a liposome, including a step of mixing an oil phase with at least one lipid dissolved in an organic solvent and a water phase and stirring an aqueous solution containing the lipids, and a step of evaporating the organic solvent from the aqueous solution containing the liposomes obtained in the stirring step, in which the organic solvent is a mixed solvent of a water-soluble organic solvent and an ester-based organic solvent.

18 Claims, 1 Drawing Sheet

(51) Int. Cl.
  *A61K 47/14* (2017.01)
  *B01J 13/12* (2006.01)
  *A61K 31/7068* (2006.01)
  *A61Q 19/00* (2006.01)
  *A61K 8/14* (2006.01)

(52) U.S. Cl.
  CPC ....... *A61K 2800/10* (2013.01); *Y10S 977/773* (2013.01); *Y10S 977/906* (2013.01); *Y10S 977/907* (2013.01)

(56) References Cited

U.S. PATENT DOCUMENTS

| | | | |
|---|---|---|---|
| 5,192,544 | A | 3/1993 | Grollier et al. |
| 5,234,635 | A | 8/1993 | Grollier et al. |
| 6,444,193 | B1 * | 9/2002 | Omtveit ............. B01F 7/00766 424/9.52 |
| 2009/0110643 | A1 * | 4/2009 | Maruyama ......... A61K 41/0028 424/9.51 |
| 2012/0225117 | A1 * | 9/2012 | Isoda ................. A61K 9/113 424/450 |

FOREIGN PATENT DOCUMENTS

| | | |
|---|---|---|
| JP | 06-065381 B2 | 9/1991 |
| WO | 85/000751 A1 | 2/1985 |
| WO | 2011/062255 A1 | 5/2011 |

OTHER PUBLICATIONS

PubChem: Ethanol. Retrieved from https://pubchem.ncbi.nlm.nih.gov/compound/ethanol#section=Top.*

PubChem: Ethyl Acetate. Retrieved from https://pubchem.ncbi.nlm.nih.gov/compound/8857.*

JN Israelachvili, S Marcelja, RG Horn. "Physical principles of membrane organization." Quarterly Reviews of Biophysics, vol. 13(2), 1980, pp. 121-200.*

JM Resa, JM Goenaga. "Liquid-Liquid Equilibrium Diagrams of Ethanol + Water + (Ethyl Acetate or 1-Pentanol) at Several Temperatures." Journal of Chemical Engineering Data, vol. 51, 2006, pp. 1300-1305.*

International Search Report for PCT/JP2015/062985 dated Aug. 11, 2015 [PCT/ISA/210].

Written Opinion for PCT/JP2015/062985 dated Aug. 11, 2015 [PCT/ISA/237].

Shah, Shrenik P., et al., "Liposomal Amikacin Dry Powder Inhaler: Effect of Fines on In Vitro Performance", AAPS PharmSciTech, Jan. 1, 2004, XP55328771, pp. 1-7.

Giuberti, Cristiane dos Santos, et al., "Investigation of alternative organic solvents and methods for the preparation of long-circulating and pH-sensitive liposomes containing cisplatin", J. Liposome Res., vol. 23, No. 3, 2013, pp. 220-227, XP055328745.

Cortesi, R., et al., "Short Communication Preparation of liposomes by reverse-phase evaporation using alternative organic solvents", Journal of Microencapsulation, Taylor and Francis, Basingstoke, GB, vol. 16, No. 2, Mar. 1, 1999, pp. 251-256, XP000800810.

Extended European Search Report dated Jan. 16, 2017, from the European Patent Office in counterpart European Application No. 15785778.0.

International Preliminary Report on Patentability and Written Opinion of the International Searching Authority dated Nov. 10, 2016 in counterpart International Application No. PCT/JP2015/062985.

* cited by examiner

METHOD FOR PRODUCING LIPOSOME

CROSS-REFERENCE TO RELATED APPLICATIONS

The present application is a continuation of PCT/JP2015/062985 filed on Apr. 30, 2015 and claims priority under 35 U.S.C. § 119 of Japanese Patent Application No. 94142/2014 filed on Apr. 30, 2014.

BACKGROUND OF THE INVENTION

1. Field of the Invention

The present invention relates to a method for producing a liposome. More specifically, the present invention relates to a method for producing a liposome which can be preferably used for pharmaceutical applications.

2. Description of the Related Art

A liposome (hereinafter, also referred to as lipid vesicle) is a closed vesicle formed of a lipid bilayer membrane using lipids, and has a water phase (inner water phase) within the space of the closed vesicle. Liposomes are usually present in a state of being dispersed in an aqueous solution (outer water phase) outside the closed vesicle. Liposomes have been studied for a variety of applications such as immune sensors, artificial red blood cells, and carriers of drug delivery systems taking advantage of features such as barrier capacity, compound retention capacity, biocompatibility, the degree of freedom of setting the particle size, ready biodegradability, and surface-modifying properties. In carrier applications, liposomes can encapsulate water-soluble compounds, lipophilic low-molecular weight materials, polymers and a wide range of materials.

In the case where liposomes are used particularly as a carrier for a drug delivery system, it is necessary to make a particle size be about 200 nm or less in terms of permeation through a biological membrane. Further, in a carrier for a drug delivery system, it is also necessary to have liposomes which form particles having a good dispersibility under the temperature conditions of about 37° C. which is the body temperature of a mammal. In particular, with regard to nano-sized fine particles, it is preferred to impart preservation stability from various viewpoints such as aggregation, precipitation, and leakage of drugs.

As a carrier for a drug delivery system, in the case where a drug (solution or the like containing liposomes containing a drug) is administered by intravenous injection, high safety is required for an intravenous injection product. Additives such as chlorinated solvents, for example chloroform, or dispersing aids whose use are not allowed are undesirable. In addition, impartment of stability as a pharmaceutical product is also necessary, and correspondingly suppression of pharmaceutical leakage, lipid decomposition or the like after storage is required. Further, suitability for sterile filtration is also required in order to guarantee sterility. When it is desired to produce liposomes as a pharmaceutical product on an industrial scale, it is necessary to take into account the requirements as described above.

For example, the industrial scale production method of liposomes may be an emulsification method. JP1994-65381B (JP-H06-65381B) discloses a method for producing an aqueous dispersion liquid of lamellar lipid vesicles, including a step of adding a solution where at least one lipid was dissolved in at least one organic solvent at a temperature of about 35° C. to 55° C. to a water phase, a step of stirring to disperse the resulting mixture, and further a step of evaporating the organic solvent together with a portion of water in the solvent. The organic solvent is immiscible with water, and an amount of each of two phases in this method is adjusted so that an oil-in-water (O/W) dispersion liquid is obtained. Further, it is surmised that liposome formation is achieved as stirring is vigorously carried out such that the continuous phase of the dispersion liquid is always a water phase. However, since the method described in JP1994-65381B (JP-H06-65381B) employs chlorinated organic solvents such as dichloromethane and chloroform, as water-immiscible organic solvents, it may be necessary to cope with the safety problems of the working conditions and liposomes to be produced. Further, in this method, if it is desired to form stable vesicles, the addition of a stabilizer other than lipids or a sizing process may be required from the viewpoint of achieving a finer particle size.

JP1996-24840B (JP-H08-24840B) discloses a method for preparing a submicron-sized liposome by adding amphiphilic lipids dissolved in ethanol to a water phase while stirring the water phase with a magnetic stirrer. According to this method, it is possible to make liposomes by adding drug active ingredients or drug precursors, biological reagents or cosmetics to a water phase or an organic phase.

However, amphiphilic lipids are limited to those that are soluble in ethanol, and applicable phospholipids are only lecithins. Thus, it is difficult to prepare liposomes in which various phospholipids are mixed in an arbitrary ratio. Further, since the particle size is increased with removal of a solvent in this method, processing using a membrane filter having uniform pores or the like is required in order to align a particle size.

JP1995-68119B (JP-H07-68119B) discloses a method for forming a liposome by dissolving phospholipids in an organic solvent which can be mixed with an aqueous component, such as alcohol, mixing and dispersing the phospholipids in a sufficient amount of the aqueous component to make a single phase and then evaporating the solvent to form a lipid thin membrane, adding an aqueous component to the lipid thin film and stirring the resulting mixture to form a liposome. Although it has been described that a stable liposome suitable for injection can be produced by this method, there is no description for the particle size and dispersion stability of the liposomes produced.

Although WO2011/062255A discloses a method for forming fine particles by two steps of an emulsifying step and a solvent removing step using a mixed solvent containing at least two organic solvents, two solvent groups, that is, solvent group A consisting of hydrocarbons and solvent group B consisting of ester, alcohol, ether, chlorinated solvents such as chloroform, and the like are used in combination. Solvents which have a risk of effects on the human body, such as hexane or chloroform are used. Further, there is also a description that a dispersant undesirable as an injection, such as Pluronic, is used for the purpose of miniaturization. In the case where these dispersants are not used, the particle size is about 135 nm which cannot be said to be sufficient for the formation of fine particles of 100 nm or less. Further, there is no description of preservation stability required for pharmaceutical products.

Generally, surfactants such as a dispersant (in the present invention, the dispersant also includes a dispersion aid) effectively lower the interfacial tension, and are therefore useful for miniaturization in an emulsifying step. However, the dispersant is present on at least one surface of hydrophilic and hydrophobic surfaces, and thus may facilitate leakage of a drug due to diffusion of an encapsulated drug. In addition, only a little material for the dispersant has been approved for use as an intravenous injection from the viewpoint of safety.

Further, in the case of subjecting liposomes to sizing processing, for example, extrusion processing is a method of extruding a mixture containing liposomes from fine holes of a filter using an extruder to thereby prepare liposomes. Although liposomes with a fine particle size and small size variation are obtained according to this method, there may be cases where filter clogging of an extruder, deformation of liposomes, or the like occurs, and therefore sizing processing is not preferable for efficient production of liposomes on an industrial scale.

In all of the above-mentioned documents, there is almost no report confirming the actual practically required long-term preservative property. A method for producing a liposome having safety and stability has not been fully established, and correspondingly improvements are desired.

SUMMARY OF THE INVENTION

The present invention has been made in view of the foregoing circumstances, and an object of the present invention is to provide a method for producing a liposome having safety and stability. Another object of the present invention is to provide a method for producing a liposome having safety and stability, a specific average particle size and uniform particle size distribution.

The present inventors have found that a fine and homogeneous liposome encapsulating a drug and having high preservation stability can be prepared without using organic solvents or additives having a risk of safety as an injection, by using a method for producing a liposome, comprising:

a step of mixing an oil phase with at least one lipid dissolved in an organic solvent and a water phase and stirring an aqueous solution containing the lipids; and a step of evaporating an organic solvent from the aqueous solution containing liposomes obtained in the stirring step, wherein the organic solvent is a mixed solvent of a water-soluble organic solvent and an ester-based organic solvent. The present invention has been completed based on such a finding.

In the present invention, the following aspects are preferred.

Preferably, the ester-based organic solvent is at least one selected from ethyl acetate, methyl acetate, isopropyl acetate, t-butyl acetate, or methyl propionate.

Preferably, the ester-based organic solvent is ethyl acetate.

Preferably, the water-soluble organic solvent is alcohols.

Preferably, the alcohol is at least one selected from ethanol, methanol, 2-propanol, or t-butanol.

Preferably, a mass ratio of water-soluble organic solvent: ester-based organic solvent is 90:10 to 30:70.

Preferably, the step of stirring imparts shearing at a circumferential speed of 20 m/sec or more to an aqueous solution containing lipids.

Preferably, the step of evaporating an organic solvent evaporates the organic solvent by heating.

Preferably, in the step of evaporating an organic solvent, the concentration of an organic solvent contained in an aqueous solution containing liposomes is to be 15 mass % or less within 30 minutes from after the start of a step of evaporating an organic solvent.

According to the method for producing a liposome of the present invention, it is possible to provide a liposome which does not use an undesirable organic solvent such as chloroform, methylene chloride, hexane, or cyclohexane, or an additive such as a dispersing aid that is not approved for use in intravenous injection in pharmaceutical applications, is particularly suitable for pharmaceutical use, and which has an average particle size of 200 nm or less, uniform particle size distribution, and excellent preservation stability.

Further, according to another aspect of the production method of the present invention, it is possible to provide a liposome having good production suitability (for example, sterile filtration suitability, or the like), an average particle size of 200 nm or less, uniform particle size distribution, and also excellent preservation stability.

Further, according to still another aspect of the production method of the present invention, it is possible to efficiently produce a liposome which is capable of achieving all of an average particle size and particle size distribution, production suitability (for example, production of homogeneous and fine liposomes without sizing processing, sterile filtration suitability, or the like), and preservation stability required for a formulation, which are suitable for pharmaceutical use, on an industrial scale.

DESCRIPTION OF THE PREFERRED EMBODIMENTS

The term "step" as used herein includes not only an independent step, but also a step which may not be clearly separated from another step, insofar as an expected effect of the step can be attained.

The numerical value ranges shown with "to" in the present specification means ranges including the numerical values indicated before and after "to" as the minimum and maximum values, respectively.

In the present invention, unless otherwise specified, % means mass percent.

In referring herein to a content of a component in a composition, in a case where plural substances exist corresponding to a component in the composition, the content means, unless otherwise specified, the total amount of the plural substances existing in the composition.

Hereinafter, the present invention will be described in detail.

The present invention is a method for producing a liposome, including:

a step of mixing an oil phase with at least one lipid dissolved in an organic solvent and a water phase and stirring an aqueous solution containing the lipids; and a step of evaporating an organic solvent from the aqueous solution containing liposomes obtained in the stirring step, in which the organic solvent is a mixed solvent of a water-soluble organic solvent and an ester-based organic solvent.

(Liposome)

The liposome is a closed vesicle formed of a lipid bilayer membrane using lipids, and has a water phase (inner water phase) within the space of the closed vesicle. The inner water phase contains water and the like. The liposome is usually present in a state of being dispersed in an aqueous solution (outer water phase) outside the closed vesicle. The liposome may be single lamellar (which is also referred to as monolayer lamellar or unilamellar, and is a structure having a single bilayer membrane) or multilayered lamellar (which is also referred to as multilamellar and is an onion-like structure having multiple bilayer membranes where individual layers are compartmented by aqueous layers). In the present invention, a single lamellar liposome is preferred from the viewpoint of safety and stability in pharmaceutical applications.

The liposome is not particularly limited in terms of form as long as it is a liposome capable of encapsulating a drug or the like. The "encapsulating" means that a drug or the like takes a form such as encapsulation, enclosure or deposition with respect to the liposome. For example, the liposome may be a form where a drug or the like is enclosed within a closed space formed of a membrane, a form where a drug or the like is encapsulated in the membrane itself, a form where a drug is deposited on the surface of a liposome (for example, a form where a drug is present on at least one surface of an outer membrane surface and an inner membrane surface of a lipid bilayer) or a combination thereof.

The size (average particle size) of a liposome is not particularly limited, and it is 2 to 200 nm, preferably 5 to 150 nm, more preferably 5 to 120 nm, and still more preferably 5 to 100 nm. In the present invention, the "average particle size" means an average value of diameters of liposomes as measured by a light scattering method.

The liposome is preferably in the form of a spherical shape or a morphology close thereto.

The component (membrane component) constituting the lipid bilayer of a liposome is selected from lipids. As the lipid, any one may be used as long as it is dissolved in a mixed solvent of a water-soluble organic solvent and an ester-based organic solvent. Specific examples of lipids include phospholipids, lipids other than phospholipids, cholesterols and derivatives thereof. These components may be composed of single or plural components.

Examples of the phospholipid include natural or synthetic phospholipids such as phosphatidylcholine (lecithin), phosphatidyl glycerol, phosphatidic acid, phosphatidyl ethanolamine, phosphatidyl serine, phosphatidyl inositol, sphingomyelin, and cardiolipin, or hydrogenated products thereof (for example, hydrogenated soybean phosphatidylcholine (HSPC)). Among these, preferred is a hydrogenated phospholipid such as hydrogenated soybean phosphatidylcholine, or sphingomyelin, and more preferred is hydrogenated soybean phosphatidylcholine. In the present invention, the "phospholipid" also encompasses a phospholipid derivative in which the phospholipid is modified.

Lipids other than phospholipids may be lipids containing no phosphoric acid, and examples thereof include, but are not particularly limited to, glycerolipid which does not contain a phosphoric acid moiety in the molecule, and sphingolipid which does not contain a phosphoric acid moiety in the molecule. In the present invention, the term "lipids other than phospholipids" also encompasses derivatives of lipids other than phospholipids in which modifications have been made to lipids other than phospholipids.

In the case where the lipid other than phospholipid contains a basic functional group, for example, in the case where the lipid other than phospholipid is a material where a compound having a basic functional group is bonded to a lipid, the lipid is referred to as a cationized lipid. The cationized lipid, for example, becomes possible to modify the membrane of the liposome and therefore can enhance the adhesiveness to cells which are target sites.

Examples of the cholesterols include cholesterol. When the average particle size decreases to 100 nm or less, the curvature of the lipid membrane becomes higher. Since the deformation of the membrane arranged in the liposome also becomes larger, a water-soluble drug becomes more susceptible to leakage. However, as a means for suppressing leakage properties, it is effective to add cholesterol or the like in order to fill the deformation of the membrane caused by lipid.

In addition to the above-mentioned components, a hydrophilic polymer or the like for improving retentivity in blood, fatty acid, diacetyl phosphate or the like as a membrane structure stabilizer, or α-tocopherol or the like as an antioxidant may be added to the liposome. In the present invention, it is preferable not to use additives such as a dispersing aid not authorized for intravenous injection use in pharmaceutical applications, for example, a surfactant or the like.

The liposome of the present invention preferably may contain hydrophilic polymer-modified products of phospholipids, lipids other than phospholipids, or cholesterols as phospholipids, lipids other than phospholipids, cholesterols and derivatives thereof.

Examples of the hydrophilic polymer include, but are not particularly limited to, polyethylene glycols, polyglycerols, polypropylene glycols, polyvinyl alcohols, a styrene-maleic anhydride alternating copolymer, polyvinylpyrrolidone, and synthetic polyamino acid. The above-mentioned hydrophilic polymers may be used alone or in combination of two or more thereof.

Among these, from the viewpoint of retentivity in blood of a formulation, preferred are polyethylene glycols, polyglycerols, or polypropylene glycols, and more preferred is polyethylene glycol (PEG), polyglycerol (PG), or polypropylene glycol (PPG). Polyethylene glycol (PEG) is most commonly used and is preferable due to having an effect of improving retentivity in blood.

The molecular weight of PEG is not particularly limited. The molecular weight of PEG is 500 to 10,000 daltons, preferably 1,000 to 7,000 daltons, and more preferably 2,000 to 5,000 daltons.

In the liposome of the present invention, it is preferable to use a lipid modified by PEG (PEG-modified lipid), together with the main lipid contained in the liposome. Examples of the PEG-modified lipid include 1,2-distearoyl-3-phosphatidylethanolamine-polyethylene glycol such as 1,2-distearoyl-3-phosphatidylethanolamine-PEG2000 (manufactured by Nippon Oil & Fats Co., Ltd.), 1,2-distearoyl-3-phosphatidylethanolamine-PEG5000 (manufactured by Nippon Oil & Fats Co., Ltd.) and distearoyl glycerol-PEG2000 (manufactured by Nippon Oil & Fats Co., Ltd.). These PEG-modified lipids may be added in an amount of 0.3 to 50 mass %, preferably 0.5 to 30 mass %, and more preferably 1 to 20 mass % with respect to total lipid content.

In the liposome of the present invention, preferred is a lipid combination of hydrogenated soybean phosphatidylcholine (a main lipid contained in liposome), 1,2-distearoyl-3-phosphatidylethanolamine-polyethylene glycol (a lipid used in combination with the main lipid), and cholesterol.

(Drug)

The liposome of the present invention may contain at least one of a water-soluble drug or a lipid-soluble drug as a drug.

In the case of a lipid-soluble drug, there is an advantage in that the drug can be relatively easily retained in the lipid membrane by hydrophobic interactions or in that it is easy to prepare a formulation which does not leak a drug due to being not soluble in water.

In the case of a water-soluble drug, a form to be retained in the inner water phase of the liposome is advantageous, but there may be a case where a drug becomes readily susceptible to leakage because the lipid bilayer membrane is thin and soft. However, according to the method for producing a liposome of the present invention, it is possible to produce a liposome having safety and stability since the particle size of the liposome can be made about 200 nm or less. Therefore, in the present invention, the drug that can be encapsulated in liposomes is preferably a water-soluble drug.

The drug which is an active ingredient capable of being encapsulated in liposomes is not particularly limited, and specific examples thereof include materials having a physiological activity or a pharmacological activity such as enzymes, proteins, peptides, nucleic acids, low-molecular weight compounds, sugars (oligosaccharides and polysaccharides), and polymer compounds. In the case where liposomes are used as a carrier for a drug delivery system, the drug is preferably a low-molecular weight compound, and more preferably a water-soluble low-molecular weight compound, from the viewpoint of stability. The drug may be formulated into a water-soluble drug or lipid-soluble pharmaceutical preparation by optionally adding additives or the like to a water-soluble drug or lipid-soluble drug.

Specific examples of the low-molecular weight compound drug include anticancer agents such as an anthracycline-based anticancer agent such as doxorubicin, daunorubicin or epirubicin, a cisplatin-based anticancer agent such as cisplatin or oxaliplatin, a taxane-based anticancer agent such as paclitaxel or docetaxel, a *vinca* alkaloid-based anticancer agent such as vincristine or vinblastine, a bleomycin-based anticancer agent such as bleomycin, and a sirolimus-based anticancer agent such as sirolimus, and metabolic antagonists such as methotrexate, fluorouracil, gemcitabine, cytarabine, and pemetrexed. Among these, preferred is a water-soluble drug such as doxorubicin, gemcitabine, or pemetrexed.

(Method for Producing Liposome)

The method for producing a liposome according to the present invention includes a step of mixing an oil phase with at least one lipid dissolved in an organic solvent and a water phase and stirring an aqueous solution containing the lipids (hereinafter, sometimes referred to as stirring step) and a step of evaporating an organic solvent from the aqueous solution containing liposomes obtained in the stirring step (hereinafter, sometimes referred to as evaporating step). The method for producing a liposome may include, if desired, other steps, in addition to the stirring step and the evaporating step.

(Oil Phase)

As the organic solvent serving as an oil phase, a mixed solvent of a water-soluble organic solvent and an ester-based organic solvent is used. In the present invention, it is preferred that an organic solvent such as chloroform, methylene chloride, hexane, or cyclohexane is not substantially used as the organic solvent, and it is more preferred that these organic solvents are not used at all.

The water-soluble organic solvent is not particularly limited, and it is preferably an organic solvent having a property that is optionally miscible with water. Specific examples of the water-soluble organic solvent include alcohols such as methanol, ethanol, n-propanol, isopropanol, n-butanol, isobutanol, and t-butanol; glycols such as glycerol, ethylene glycol, and propylene glycol; and polyalkylene glycols such as polyethylene glycol. Among these, preferred are alcohols. The alcohol is preferably at least one selected from ethanol, methanol, isopropanol, or t-butanol, more preferably at least one selected from ethanol, isopropanol, or t-butanol, and still more preferably ethanol.

The ester-based organic solvent is not particularly limited, and it is preferably an ester obtained from the reaction of organic acids and alcohols. Specifically, the ester-based organic solvent is preferably at least one selected from ethyl acetate, methyl acetate, isopropyl acetate, t-butyl acetate, or methyl propionate, more preferably ethyl acetate, isopropyl acetate, or methyl propionate, and still more preferably ethyl acetate.

The mixing ratio of water-soluble organic solvent:ester-based organic solvent is not particularly limited, and it may be 90:10 to 30:70, preferably 80:20 to 40:60, and more preferably 80:20 to 70:30 by mass ratio. The mixed solvent of a water-soluble organic solvent and an ester-based organic solvent may further contain an aqueous solvent to be described below, such as water or buffer. The aqueous solvent may be added in a range of, for example, 1 to 30 mass %. The pH of the mixed solvent is not particularly limited, and it is preferably in the range of about 3 to 10, and more preferably about 4 to 9. The ester-based organic solvents may contain physiologically active substances or the like such as various medicines which are soluble in these solvents.

In the case where ethanol is used as the water-soluble organic solvent and ethyl acetate is used as the ester-based organic solvent, the mixing ratio of ethanol:ethyl acetate is not particularly limited, and it is preferably 80:20 to 70:30 by a mass ratio.

The concentration of the lipid is not particularly limited and may be appropriately adjusted, but it may be 40 g/L to 250 g/L, preferably 40 g/L to 200 g/L in terms of a solution where a mixed solution of a water-soluble organic solvent and an ester-based organic solvent serves as a solvent.

(Water Phase)

The water phase means an outer water phase and an inner water phase.

The outer water phase as used herein means an aqueous solution in which the liposomes are dispersed. For example, in the case of an injection, a solution occupying the outside of the liposome of a dispersion liquid of liposomes packaged and stored in a vial or prefilled syringe becomes an outer water phase. Also, similarly for a liquid to be dispersed at the time of use when administered by means of an attached dispersion solution or other solutions, a solution occupying the outside of the liposome of a dispersion liquid of liposomes becomes an outer water phase.

The inner water phase as used herein means a water phase in the closed vesicle with a lipid bilayer membrane therebetween.

As a liposome-dispersing aqueous solution (outer water phase) when producing liposomes, water (distilled water, water for injection, or the like), physiological saline, various buffers, an aqueous solution of sugars or a mixture thereof (aqueous solvent) is preferably used. The buffer is not limited to organic and inorganic buffer solutions, and a buffer having a buffering action in the vicinity of a pH close to that of the body fluid is preferably used and examples thereof include phosphate buffer, tris buffer, citrate buffer, acetate buffer, and Good's buffer. The pH of the water phase is not particularly limited, and it may be 5 to 9, preferably 7 to 8. For example, a phosphate buffer (for example, pH=7.4) is preferably used. The inner water phase of the liposome may be a liposome-dispersing aqueous solution when producing liposomes, or may be water, physiological saline, various buffers, an aqueous solution of sugars or a mixture thereof which are newly added. The water used as an outer water phase or an inner water phase is preferably free from impurities (dust, chemicals, or the like).

The physiological saline refers to an inorganic salt solution adjusted to be isotonic with the human body fluid, and may further have a buffering function. Examples of the physiological saline include saline containing 0.9 w/v % of sodium chloride, phosphate buffered saline (hereinafter, also referred to as PBS), and tris buffered saline.

(Stirring Step)

In the stirring step, an oil phase where at least one lipid has been dissolved in an organic solvent and a water phase are mixed and the aqueous containing lipids are stirred. An oil phase where lipids have been dissolved in an organic solvent and a water phase are mixed and stirred to thereby prepare an emulsion where an oil phase and a water phase are emulsified in an O/W type. After mixing, a liposome is formed by removing a portion or all of the organic solvent derived from the oil phase using an evaporating step to be described below. Alternatively, a portion or all of the organic solvent in the oil phase is evaporated in the course of the stirring-emulsification to form a liposome.

As a method of stirring, ultrasonic waves or mechanical shearing force is used for particle miniaturization. In addition, extruder processing of allowing to pass through a filter having a certain pore diameter or microfluidizer processing may be carried out for uniformity of particle sizes. However, in the production method of the present invention, it is preferred that sizing processing is not carried out since the liposomes are miniaturized.

In the present invention, an average particle size of a liposome to be prepared can be controlled by arbitrarily selecting the speed and time of stirring. In view of obtaining a liposome having safety and stability, it is preferable to provide shearing at a circumferential speed of 20 m/sec or higher to an aqueous solution containing lipids. The shearing is not limited, and a specific example thereof is preferably shearing at a circumferential speed of 20 m/sec to 35 m/sec, and more preferably shearing at a circumferential speed of 23 m/sec to 30 m/sec.

(Evaporating Step)

In the evaporating step, an organic solvent is evaporated from the aqueous solution containing liposomes obtained in the stirring step. In the present invention, the evaporating step includes at least one of a step of forcibly removing a portion or all of the organic solvent derived from the oil phase as an evaporating step, and a step of naturally evaporating a portion or all of the organic solvent in the oil phase during the course of stirring-emulsification.

The method of evaporating an organic solvent in the evaporating step is not particularly limited. For example, at least one of a step of heating to evaporate an organic solvent, a step of continuing the standing or slow stirring after emulsification, or a step of performing vacuum degassing may be carried out.

In the present invention, in the step of evaporating an organic solvent, it is preferred that the concentration of an organic solvent contained in an aqueous solution containing liposomes is to be 15 mass % or less within 30 minutes from after the start of a step of evaporating the organic solvent.

A liquid temperature when carrying out the production method of the present invention can be appropriately adjusted, but the liquid temperature at the time of mixing an oil phase and a water phase is preferably higher than or equal to a phase transition temperature of the lipid to be used. For example, in the case where a lipid having a phase transition temperature of 35° C. to 40° C. is used, the liquid temperature is preferably set to 35° C. to 70° C.

The aqueous solution containing the liposomes prepared via an stirring step and an evaporating step may be subjected to post-processing such as centrifugation, ultrafiltration, dialysis, gel filtration, or freeze-drying, for removal of components that had not been included in the liposomes, or adjustment of a concentration and an osmotic pressure.

(Sterile Filtration)

In order to formulate an aqueous solution containing liposomes, obtained by the method for producing a liposome according to the present invention, into a pharmaceutical product, it is preferable to carry out sterile filtration. Regarding the filtration method, it is possible to remove unwanted materials from the aqueous solution containing liposomes by using a hollow fiber membrane, a reverse osmosis membrane, a membrane filter or the like. In the present invention, the aqueous solution containing liposomes is preferably filtered by means of a filter having a sterile pore size (preferably 0.2 µm sterile filter) although there is no particular limitation. Normally, adsorption or aggregation of liposomes onto a sterile filter may occur in the filtration step. However, the present invention has unexpected effects such as little influence of pressure loss or the like when performing filtration, since liposomes having a specific average particle size and uniform particle size distribution are obtained.

To prevent an effect of liposome deformation on the average particle size, the sterile filtration step and the below-described aseptic filling step are preferably carried out at a temperature lower than or equal to the phase transition temperature of the lipid constituting the liposome. For example, in the case where the phase transition temperature of the lipid is around 50° C., the sterile filtration step and the below-described aseptic filling step are carried out at temperature of preferably about 0° C. to 40° C., and more specifically about 5° C. to 30° C.

(Aseptic Filling)

The aqueous solution containing the liposomes obtained after sterile filtration is preferably aseptically filled for medical applications. Known methods can be applied for aseptic filling. A liposome formulation suitable for medical applications can be prepared by aseptically filling the liposome-containing aqueous solution in a container.

An aqueous solvent, an additive, or the like may be appropriately added to the aqueous solution containing the liposomes obtained by the present invention to thereby prepare a liposome formulation. In connection with the route of administration, the liposome formulation may also contain at least one of a stabilizer, an antioxidant, or a pH adjusting agent which is pharmaceutically acceptable.

The stabilizer is not particularly limited and examples thereof include sugars such as glycerol, mannitol, sorbitol, lactose, and sucrose.

The antioxidant is not particularly limited and examples thereof include ascorbic acid, uric acid, tocopherol homologues (for example, vitamin E, four tocopherol isomers α, β, γ, and δ), cysteine, and EDTA. Stabilizers and antioxidants may be respectively used alone or in combination of two or more thereof.

Examples of the pH adjusting agent include sodium hydroxide, citric acid, acetic acid, triethanolamine, sodium hydrogen phosphate, and sodium dihydrogen phosphate.

The liposome formulation of the present invention may contain an organic solvent, collagen, polyvinyl alcohol, polyvinyl pyrrolidone, a carboxyvinyl polymer, sodium carboxymethyl cellulose, sodium polyacrylate, sodium alginate, water-soluble dextran, sodium carboxymethyl starch, pectin, methyl cellulose, ethyl cellulose, xanthan gum, gum arabic, casein, gelatin, agar, diglycerol, propylene glycol, polyethylene glycol, vaseline, paraffin, stearyl alcohol, stearic acid, human serum albumin (HSA), mannitol, sorbitol, lactose, PBS, sodium chloride, sugars, a biodegradable polymer, a serum-free medium, each of which is pharmaceutically acceptable, or an additive which is acceptable as a pharmaceutical additive.

In particular, in the context of the present invention, the liposome formulation preferably contains ammonium sulfate, L-histidine, purified sucrose, sodium hydroxide, hydrochloric acid, or the like.

The container in which a liposome formulation is filled is not particularly limited, and it is preferably made of a material having low oxygen permeability in order to prevent oxidation or the like. Examples of the container include a plastic container, a glass container, and a bag made of a laminate film having an aluminum foil, an aluminum-deposited film, an aluminum oxide-deposited film, a silicon oxide-deposited film, a polyvinyl alcohol, an ethylene-vinyl alcohol copolymer, polyethylene terephthalate, polyethylene naphthalate, polyvinylidene chloride, or the like as a gas barrier layer. If necessary, light may be shielded by adopting a bag or the like using a colored glass, an aluminum foil, aluminum-deposited film or the like.

In the container in which a liposome formulation is filled, in order to prevent oxidation by oxygen present in the space in the container, it is preferable to replace gases in the container space and drug solution with inert gases such as nitrogen. For example, an injection solution is bubbled with nitrogen, whereby the filling of the injection solution into a container can be carried out under a nitrogen atmosphere.

The administration method of a liposome formulation is preferably parenteral administration. For example, intravenous injection such as intravenous drip, intramuscular injection, intraperitoneal injection, or subcutaneous injection may be selected. The specific administration method of a liposome formulation includes, for example, a syringe, and administration by intravenous drip.

The dose of a drug contained in the liposome formulation is usually selected in the range of 0.01 mg to 100 mg/kg body weight/day. However, the liposome formulation of the present invention is not limited to such a dose.

(Method for Measuring Particle Size of Liposomes)

In the method for producing a liposome of the present invention, it is possible to produce fine and homogeneous liposomes. An example of the method for measuring a particle size of liposomes includes a dynamic light scattering method.

With regard to the dynamic light scattering method, it is generally known that a particle size can be obtained with good accuracy in a solution of dilute particle concentration. That is, in the case where the particle concentration in a solution is high, there may be a case where the influence of multiple scattering (phenomenon where scattered light is dispersed again by being hit against other particles) cannot be ignored. However, diluting the aqueous solution containing liposomes obtained in the present invention may result in a case where a value of a particle size in an actual solution cannot be obtained correctly. In addition, upon industrialization of a formulation, there is a case where the presence of slight coarse particles may significantly affect foreign substance removal and filter permeability at the time of sterile filtration, but dilution of the liposome-containing aqueous solution may lead to difficulty of detecting such slight coarse particles in many cases.

Although the measurement of a particle size of the liposomes according to the present invention may also employ a dynamic light scattering measuring apparatus according to a Michelson interferometer, it is preferable to use a low-coherence dynamic light-scattering measuring apparatus according to a Mach-Zehnder type interferometer, which can measure an actual particle size and particle size distribution of liposomes with good accuracy even when a particle concentration is high. Accordingly, effects of multiple scattering are suppressed, so the particle size and particle size distribution can be measured with good accuracy, without diluting a solution containing liposomes. In particular, with regard to the detection of coarse particles, it is possible to suitably use such a measuring method with very high sensitivity. For example, a measurement may be carried out by referring to JP5325679B.

INDUSTRIAL APPLICABILITY

According to the method for producing a liposome of the present invention, it is possible to provide a liposome which has an average particle size of 200 nm or less, and which is also excellent in preservation stability. The liposomes obtained by the method for producing a liposome of the present invention are applicable for pharmaceuticals, cosmetics, foodstuff, or the like, and are particularly useful for pharmaceutical applications.

EXAMPLES

Hereinafter, the present invention will be described in detail with reference to Examples. However, the present invention is not limited to such Examples.

The mixing ratio in the solvent composition refers to a volume ratio. For example, "ethanol/ethyl acetate=90/10" refers to 90% ethanol/10% ethyl acetate by a volume ratio.

Example 1 a) Preparation of Oil Phase

Hydrogenated soybean phosphatidylcholine, cholesterol and N-(carbonyl-methoxypolyethylene glycol 2000)-1,2-distearoyl-sn-glycero-3-phosphoethanolamine sodium salt (hereinafter, also referred to as DSPE-PEG) were mixed in a molar ratio of 57/38/5, and then an organic solvent (ethanol/ethyl acetate=75/25) was added thereto, followed by warming to 70° C. and dissolving the lipids to prepare an oil phase.

b) Preparation of Water Phase 177 mM of an aqueous ammonium sulfate solution was prepared to serve as a water phase.

c) Emulsification

The water phase prepared in b) was warmed to 70° C., and the oil phase prepared in a) was added such that a volume ratio of water phase/oil phase=8/3 is achieved, followed by stirring at circumferential speed of 30 m/s and angular velocity of 19000 rpm for 30 minutes.

d) Desolvation

The organic solvent was removed by blowing with nitrogen while warming the emulsion prepared in c) to a temperature higher than or equal to the phase transition temperature of the lipids. Then, nitrogen blowing was stopped, followed by warming to a temperature higher than or equal to the phase transition temperature of the lipids for 3 hours to obtain liposomes.

Example 2

Liposomes were obtained in the same manner as in Example 1, except that the composition of an organic solvent used for the preparation of liposomes was changed from (ethanol/ethyl acetate=75/25) to (ethanol/ethyl acetate=90/10).

Example 3 a) Preparation of Oil Phase

Hydrogenated soybean phosphatidylcholine, cholesterol and DSPE-PEG were mixed in a molar ratio of 76/19/5, and then an organic solvent (ethanol/ethyl acetate=75/25) was added thereto, followed by warming to 70° C. and dissolving the lipids to prepare an oil phase.

b) Preparation of Water Phase 4 mM phosphate buffer (pH 7.86) was prepared to serve as a water phase.

c) Preparation of Drug-Unencapsulated Liposomes

The water phase was warmed to 70° C., and the oil phase was added in such a way that a volume ratio of water phase/oil phase=8/3 is achieved, followed by stirring at circumferential speed of 20 m/s and 13000 rpm for 30 minutes. Thereafter, the organic solvent was removed by blowing with nitrogen while warming to a temperature higher than or equal to the phase transition temperature. This was further followed by complete removal of the organic solvent by replacing the outer water phase of liposomes with a 0.09% sodium chloride aqueous solution while concentrating the lipid concentration of the liposome liquid to a range of 120 to 150 mM by tangential flow filtration, thereby obtaining drug-unencapsulated liposomes.

d) Preparation of Drug-Encapsulated Liposomes

1) Preparation of PBS 81.63 g of sodium chloride, 29.01 g of disodium hydrogen phosphate 12 hydrate, and 2.29 g of sodium dihydrogen phosphate dihydrate were dissolved in 948 g of water for injection to prepare PBS.

2) Preparation of Gemcitabine-Encapsulated Liposome Liquid 7.68 g of gemcitabine hydrochloride, 31.99 g of PBS, 44.83 g of Japanese Pharmacopoeia water for injection, and 1.60 mL of 8M sodium hydroxide were mixed to prepare a drug solution. Subsequently, 17.64 mL of the drug solution, 18.00 mL of drug-unencapsulated liposomes, and 0.36 mL of 8M sodium hydroxide were mixed in each of four vials. This was followed by warming at about 70° C. for 30 minutes and then cooling to room temperature. Then, the drug liposome mixture was filtered through a sterilizing filter with a pore size of 0.2 μm, and unencapsulated gemcitabine was removed by dialytic purification of the drug liposome mixture against a 9.4% sucrose/10 mM histidine aqueous solution by tangential flow filtration. Then, the liposomes were filtered through a sterile filter with a pore size of 0.2 μm to obtain a germfree gemcitabine-encapsulated liposome liquid.

Comparative Example 1

Liposomes were obtained in the same manner as in Example 1, except that the composition of an organic solvent used for the preparation of an oil phase was changed from (ethanol/ethyl acetate=75/25) to (ethanol/ethyl acetate=100/0).

Comparative Example 2

Although the procedure was carried out in the same manner as in Example 1, except that the composition of an organic solvent used for the preparation of an oil phase was changed from (ethanol/ethyl acetate=75/25) to (ethanol/ethyl acetate=0/100), it was impossible to prepare liposomes because lipids could not be completely dissolved (could not be emulsified due to poor solubility of lipids).

1. Measurement of Average Particle Size

A sample for measurement was prepared by 13-fold diluting the liposome liquid with pure water. The particle size of the prepared sample was measured using a dynamic light scattering (DLS) apparatus (FPAR-1000AS, manufactured by Otsuka Electronics Co., Ltd.). The cumulant average particle size was adopted as a representative value of the particle size.

The results are shown in Table 1. The particle size (nm) in Table 1 shows a particle size as measured by a dynamic light scattering measuring apparatus according to a Michelson interferometer.

2. Measurement of Filterability

Figure 1:
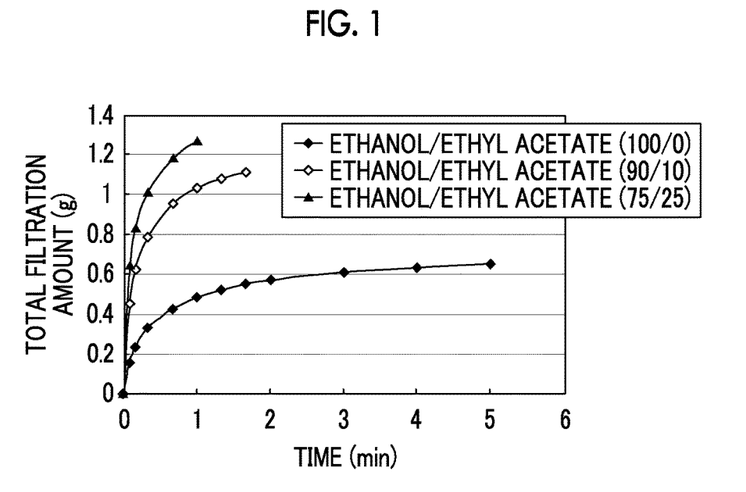
FIG. 1 is a plot of a filtration amount (g) and a time (min).

The liposome liquid was adjusted to a total lipid concentration of 25 to 30 mM and then maintained at 25° C. Water for injection was passed at 0.05 MPa through an extruder (Thermobarrel extruder, manufactured by Lipex) equipped with a 0.2 μm filter (Sartobran P, manufactured by Sartorius stedim) to wash the filter, and then the liposomes maintained at 25° C. were pressure-filtered at 0.3 MPa. The filtrate was collected and weighed at various time intervals. Filterability was calculated from the time required to filter 1 mL of the filtrate. The results are shown in Table 1 and FIG. 1. Referring to filter filterability shown in Table 1, A: filterable, B: filterable but clogging occurred, and C: non-filterable (cannot filter 1 mL). FIG. 1 shows the results of evaluating the filterability for a sample solution containing liposomes prepared by changing the ratio of ethanol/ethyl acetate. In FIG. 1, eta/ethacet refers to ethanol/ethyl acetate, and the numerical value refers to a ratio (volume ratio) for ethanol/ethyl acetate. In addition, in order to confirm whether the degree of filterability is associated with the abundance of coarse particles, a low-coherence dynamic light scattering (LC-DLS) measurement with high power of detecting coarse particles was carried out. The LC-DLS measurement was carried out as follows using a measuring apparatus composed of a Mach-Zehnder type interferometer.

Apparatus: light source SLD, wavelength 835±22 nm, AD conversion speed Max 1 μsec/ch, and immersion measurement by a fiber probe (measuring conditions are temperature of 25° C., modulation frequency of 10 kHz, sampling time 20 μsec interval 65536 points per integration, and integration of 300 times).

Analysis was carried out by Fourier transforming signals of scattered light fluctuations measured, and extracting only the modulated signal from the obtained power spectrum to calculate an autocorrelation function. The calculated autocorrelation function was converted into particle size distribution by a histogram method.

The samples to be measured were measured undiluted without any processing such as dilution. In particular, an amount of coarse materials of micron order was measured.

The results are shown in Table 1. The coarse particle percentage in Table 1 indicates an abundance ratio of coarse materials of 500 nm or more.

3. Measurement of Total Gemcitabine Content in Formulation

Using a sample solution which was obtained by dissolving the prepared liposome liquid in methanol, followed by filtration, and a calibration curve standard solution which was prepared by dilution of gemcitabine hydrochloride, a total gemcitabine content in the formulation was measured by liquid chromatography/UV-vis absorbance detection.

a) Preparation of Calibration Curve Standard Solution

About 10 mg of gemcitabine hydrochloride was weighed and dissolved in about 10 mL of 1×PBS (manufactured by Gibco, Life Technology). 1×PBS (manufactured by Gibco, Life Technology) was added thereto, and a solution having a gemcitabine hydrochloride concentration of 0.1, 1.0, 5.0, or 10.0 μg/mL was prepared and used as calibration curve standard solution.

b) Preparation of Sample Solution (1) About 50 μL of a sample (liposome formulation solution) was weighed by MICROMAN, and about 950 μL of methanol weighed by MICROMAN was added thereto. After it was shaken for about 1 minute, the solution was visually confirmed to become clear.

(2) 100 μL of the solution of the above (1) was weighed by MICROMAN, and about 950 μL of water for injection weighed by a micropipette was added thereto. This liquid was shaken for about 1 minute, sonicated for about 1 minute, and further shaken for about 10 seconds.

(3) The solution obtained by filtering the solution of the above (2) through a DISMIC filter (pore diameter: 0.45 μm) was used as a sample solution.

c) Measurement

The measurement was carried out under the following conditions by liquid chromatography/UV-vis absorbance detection.

Measurement wavelength: 272 nm, column: Waters Atlantis T3 φ4.6×150 mm, 5 μm

Column temperature: constant temperature of around 40° C.

Both of mobile phases A and B are a water/methanol/trifluoroacetic acid mixture, and feeding of the mobile phases was carried out by changing the mixing ratio of mobile phases A and B to control a concentration gradient.

Flow rate: 1.0 mL/minute, injection volume: 10 μL, autosampler temperature: constant temperature of around 25° C.

4. Measurement of Gemcitabine Amount in Outer Water Phase

Using a sample solution obtained by removing liposomes from the diluted solution of a sample (liposome formulation) by ultrafiltration, and a calibration curve standard solution which was prepared by dilution of gemcitabine hydrochloride, an gemcitabine amount in the outer water phase was measured by liquid chromatography/UV-vis absorbance detection.

a) Preparation of Sample Solution (1) About 50 μL of a sample (liposome formulation solution) was weighed by MICROMAN, and about 450 μL of PBS weighed by a micropipette was added thereto, followed by sufficient upside-down mixing to prepare a homogeneous solution.

(2) About 100 μL of the solution of the above (1) was weighed by a micropipette, and added dropwise onto a pre-washed ultrafiltration membrane which was then centrifuged. The centrifugation was carried out under the conditions of 7400×g, 30 minutes, and 5° C.

(3) The solution obtained by shaking the filtrate in the operation of the above (2) for 10 seconds was used as a sample solution.

b) Measurement

3. The measurement was carried out in the same manner as in c).

5. Preservative Property

The sample solution was stored at 5° C. for 18 months.

Using the total gemcitabine amount in the formulation measured in 3 and 4 above and the gemcitabine amount in the outer water phase, preservative leakage was calculated by the following equation.

$$\text{Preservative leakage (\%)} = 100 \times (\text{outer water phase drug concentration after 18 month storage} - \text{outer water phase drug concentration immediately after preparation of formulation}) / \text{inner water phase drug concentration} \quad \text{Equation:}$$

Further, the particle size was measured in the same manner as in 1.

The results are shown in Table 1.

TABLE 1

| | Solvent composition ethanol/ethyl acetate | Average particle size (nm) | Filterability Filter permeability | Coarse particle percentage | Preservative property Average particle size (nm) | Preservative leakage (%) |
|---|---|---|---|---|---|---|
| Example 1 | 75/25 | 83 | A | 0.1% | — | — |
| Example 2 | 90/10 | 92 | B | None | — | — |
| Example 3 | 75/25 | 80 | A | None | 82 | 0.64 |
| Comparative Example 1 | 100/0 | 138 | C | 5% | — | — |
| Comparative Example 2 | 0/100 | — | — | — | — | — |

From the results shown in Table 1, it was found that according to the production method of the present invention, it is possible to produce a liposome which does not use harmful organic solvents such as chloroform and methylene chloride and has a particle size of 200 nm or less and a single dispersion peak. Further, it was found that in Comparative Example 1, the coarse particle percentage is increased, and therefore filter permeability is significantly deteriorated. In Comparative Example 2, it was incapable of even forming liposomes. Therefore, it was found that according to the production method of the present invention, liposome particles having a particle size of 200 nm or less can also be produced to have the production suitability, such as filterability.

Examples 4-1 to 4-7

Drug-encapsulated liposomes were prepared in the same manner as in Example 3, except that the mixing ratio of organic solvents was adjusted as shown in Table 2.

The particle size of the liposomes obtained in Examples 4-1 to 4-7 was measured by the method described below.

Samples for measurement were prepared by 100-fold diluting the liposome liquid with a liquid obtained by 10-fold diluting 1×PBS (manufactured by Gibco, Life Technology) with pure water. The particle size of the prepared samples was measured using a dynamic light scattering (DLS) apparatus (FPAR-1000AS, manufactured by Otsuka Electronics Co., Ltd.). The cumulant average particle size was adopted as a representative value of the particle size.

The results are shown in Table 2.

TABLE 2

|  | Solvent composition ethanol/ethyl acetate | Average particle size (nm) |
| --- | --- | --- |
| Example 4-1 | 75/25 | 65 |
| Example 4-2 | 75/25 | 66 |
| Example 4-3 | 75/25 | 66 |
| Example 4-4 | 75/25 | 66 |
| Example 4-5 | 75/25 | 66 |
| Example 4-6 | 65/35 | 76 |
| Example 4-7 | 55/45 | 125 |

From the results shown in Table 2, it was found that the production method of the present invention is a method capable of very stably producing liposomes since there is almost no variation in the particle size of the liposome samples of Examples 4-1 to 4-5 having the same solvent composition. Although there is a tendency that the particle size is increased in Examples 4-6 and 4-7 having a higher ethyl acetate percentage in the solvent composition, it is possible to produce liposome particles having a particle size of 200 nm or less. It can be seen that the production method of the present invention is an invention which is capable of producing liposome particles having a particle size of 200 nm or less in a wide range of the solvent ratios and which is excellent in versatility.

Examples 5-1 to 5-5 a) Preparation of Oil Phase

Hydrogenated soybean phosphatidylcholine, cholesterol and DSPE-PEG were mixed in a molar ratio of 57/38/5, and then an organic solvent was added thereto, followed by warming to 70° C. and dissolving the lipids to prepare an oil phase. The ratio of an organic solvent is as follows: Example 5-1; (ethanol/ethyl acetate=88/12), Example 5-1; (ethanol/ethyl acetate=79/21), Example 5-3; (ethanol/ethyl acetate=75/25), Example 5-4; (ethanol/ethyl acetate=70/30), and Example 5-5; (ethanol/ethyl acetate=63/37).

b) Preparation of Water Phase 187 mM of an aqueous ammonium sulfate solution was prepared to serve as a water phase.

c) Preparation of Liposome Liquid by Emulsification

The water phase prepared in b) was warmed to 70° C., and the oil phase prepared in a) was added such that a volume ratio of water phase/oil phase=8/3 is achieved, followed by stirring at circumferential speed of 30 m/s and angular velocity of 19000 rpm for 30 minutes to obtain a liposome liquid.

The particle size of the liposomes obtained in Examples 5-1 to 5-5 was measured by the method described below.

Samples for measurement were adjusted by 13-fold diluting the liposome liquid with pure water. The particle size of the prepared samples was measured using a dynamic light scattering (DLS) apparatus (FPAR-1000AS, manufactured by Otsuka Electronics Co., Ltd.). The cumulant average particle size was adopted as a representative value of the particle size.

Figure 2:
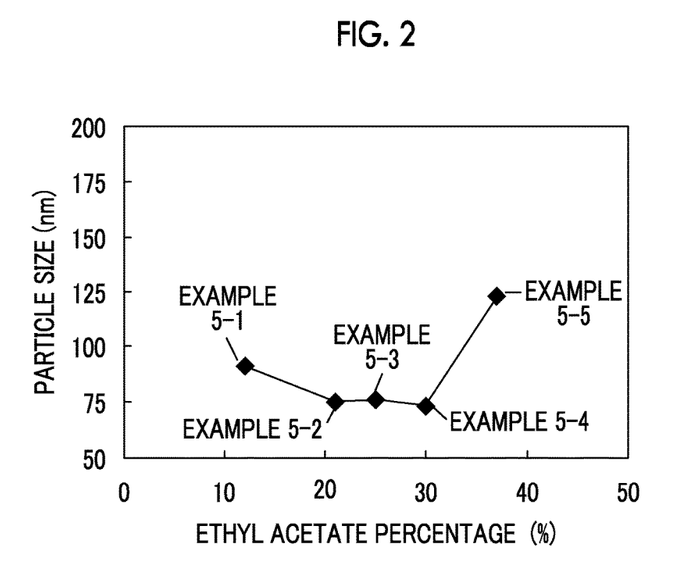
FIG. 2 is a plot of a particle size (nm) of liposomes and an ethyl acetate percentage (%).

The results are shown in Table 3 and FIG. 2.

TABLE 3

|  | Solvent composition ethanol/ethyl acetate | Average particle size (nm) |
| --- | --- | --- |
| Example 5-1 | 88/12 | 91 |
| Example 5-2 | 79/21 | 75 |
| Example 5-3 | 75/25 | 76 |
| Example 5-4 | 70/30 | 73 |
| Example 5-5 | 63/37 | 123 |

From the results shown in Table 3 and FIG. 2, it was found that according to the production method of the present invention, it is possible to produce liposome particles having a particle size of 200 nm or less. According to the production method of the present invention, ethyl acetate is preferably in the range of 20% to 30% when it is desired to achieve finer liposomes as much as possible, although it is possible to produce fine liposomes in a wide range of solvent ratios. It is considered that a small amount of ethyl acetate results in increased foaming at the time of emulsification and a loss of emulsification shear force transfer to a lipid membrane, whereas a large amount of ethyl acetate results in an increased particle size due to oil droplets of ethyl acetate being combined.

What is claimed is:

1. A method for producing liposomes, comprising:
   a step of mixing an oil phase with at least one lipid dissolved in an organic solvent and a water phase and stirring an aqueous solution containing the lipids to thereby prepare an O/W emulsion in which oil phase and water phase are emulsified;
   a step of evaporating the organic solvent from the aqueous solution containing the lipids obtained in the stirring step to form liposomes; and
   a step of sterile filtration,
   wherein the organic solvent comprises a mixture of a water-soluble organic solvent and an ester based organic solvent, wherein the water-soluble organic solvent comprises ethanol and wherein the ester-based organic solvent comprises ethyl acetate, and wherein the content of ethyl acetate is 20% to 30% by mass,
   the particle size of the liposomes is 2 to 100 nm,
   sizing processing is not carried out since the liposomes are miniaturized only by stirring step,
   the concentration of the organic solvent contained in the aqueous solution containing the lipids is 15 mass % or less within 30 minutes from after the start of the step of evaporating the organic solvent,
   the step of stirring imparts shearing at a circumferential speed of 20 m/sec or more to the aqueous solution containing lipids, and
   the concentration of the lipid is 40 g/L to 200 g/L in terms of a solution where a mixed solution of a water-soluble organic solvent and an ester-based organic solvent serves as a solvent.

2. The method for producing liposomes according to claim 1, wherein the ester-based organic solvent further includes at least one selected from methyl acetate, isopropyl acetate, t-butyl acetate, and methyl propionate.

3. The method for producing liposomes according to claim 1, wherein the ester-based organic solvent consists of ethyl acetate.

4. The method for producing liposomes according to claim 1, wherein the water-soluble organic solvent further includes one or more alcohols other than ethanol.

5. The method for producing liposomes according to claim 2, wherein the water-soluble organic solvent further includes one or more alcohols other than ethanol.

6. The method for producing liposomes according to claim 3, wherein the water-soluble organic solvent further includes one or more alcohols other than ethanol.

7. The method for producing liposomes according to claim 4, wherein the alcohol other than ethanol is at least one selected from methanol, 2-propanol, and t-butanol.

8. The method for producing liposomes according to claim 5, wherein the alcohol other than ethanol is at least one selected from methanol, 2-propanol, and t-butanol.

9. The method for producing liposomes according to claim 6, wherein the alcohol other than ethanol is at least one selected from methanol, 2-propanol, and t-butanol.

10. The method for producing liposomes according to claim 1, wherein the mass ratio of water-soluble organic solvent:ester-based organic solvent is 80:20 to 30:70.

11. The method for producing liposomes according to claim 2, wherein the mass ratio of water-soluble organic solvent:ester-based organic solvent is 80:20 to 30:70.

12. The method for producing liposomes according to claim 4, wherein the mass ratio of water-soluble organic solvent:ester-based organic solvent is 80:20 to 30:70.

13. The method for producing liposomes according to claim 1, wherein the step of evaporating the organic solvent evaporates the organic solvent by heating.

14. The method for producing liposomes according to claim 2, wherein the step of evaporating the organic solvent evaporates the organic solvent by heating.

15. The method for producing liposomes according to claim 4, wherein the step of evaporating the organic solvent evaporates the organic solvent by heating.

16. The method for producing liposomes according to claim 10, wherein the step of evaporating the organic solvent evaporates the organic solvent by heating.

17. The method for producing liposomes according to claim 1, wherein the water-soluble organic solvent consists of ethanol.

18. The method for producing liposomes according to claim 1, wherein the average particle size of the liposomes is 5 to 100 nm.

* * * * *